US00PP36282P2

(12) United States Plant Patent
Koene

(10) Patent No.: US PP36,282 P2
(45) Date of Patent: Dec. 3, 2024

(54) ***MANDEVILLA* PLANT NAMED 'Sunpa 421'**

(50) Latin Name: *Mandevilla hybrida*
Varietal Denomination: Sunpa 421

(71) Applicant: Tim Koene, Maasland (NL)

(72) Inventor: Tim Koene, Maasland (NL)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/378,104

(22) Filed: Oct. 9, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. Anne Whealy

(57) ABSTRACT

A new and distinct cultivar of *Mandevilla* plant named 'Sunpa 421', characterized by its upright and compact plant habit; vigorous growth habit; freely branching habit; early and freely flowering habit; long flowering period; double-type flowers that are purplish pink in color; and good garden performance.

2 Drawing Sheets

Figure 1:
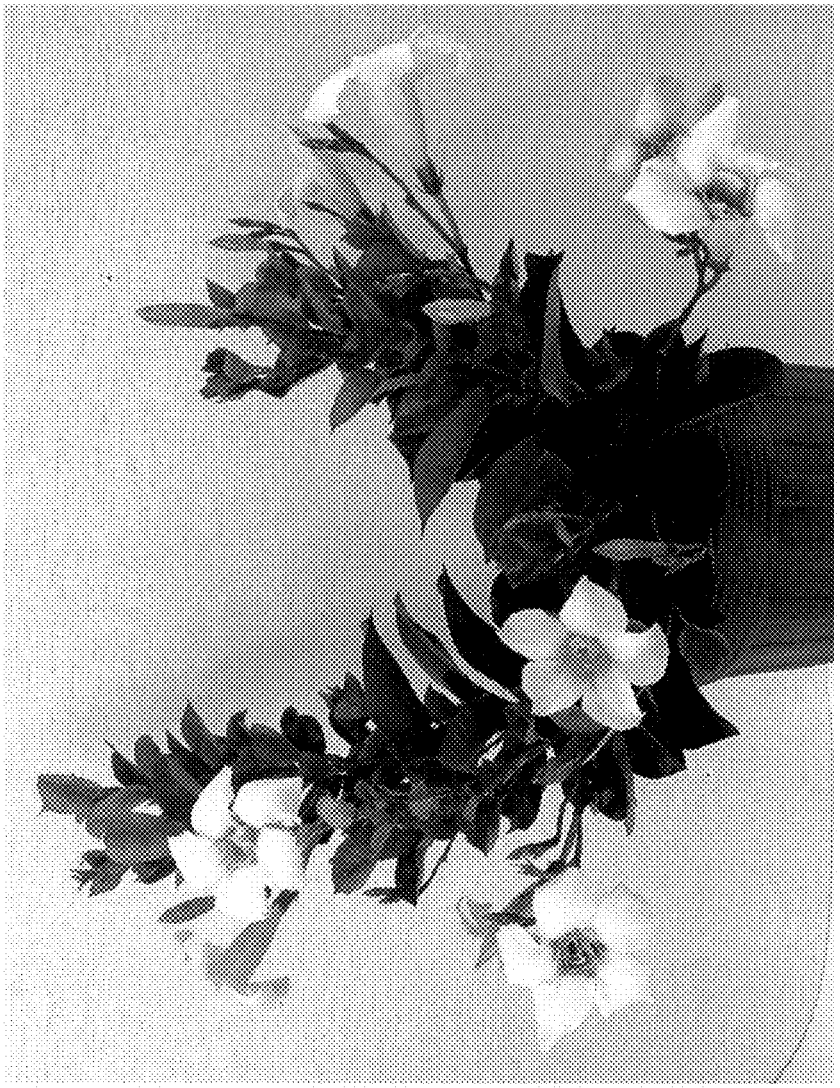

Botanical designation: *Mandevilla hybrida.*
Cultivar denomination: 'SUNPA 421'.

STATEMENT REGARDING PRIOR DISCLOSURES BY INVENTOR/APPLICANT and ASSIGNEE

An European Community Plant Breeder's Rights application for the instant plant was filed by the Assignee of the instant application, Suntory Flowers Limited of Tokyo, Japan on Jan. 5, 2022, application number 2022/0022. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 421'.

The new *Mandevilla* plant is a naturally-occurring branch mutation of a proprietary selection of *Mandevilla hybrida* identified as code number MW37-mt2, not patented. The new *Mandevilla* plant was discovered and selected by the Inventor on a single flowering plant from within a population of plants of the proprietary selection in a controlled greenhouse environment in Maasland, The Netherlands in September 2020.

Asexual reproduction of the new *Mandevilla* plant by terminal vegetative cuttings in Maasland, The Netherlands since May 2022 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 421'. These characteristics in combination distinguish 'Sunpa 421' as a new and distinct *Mandevilla* plant:

1. Upright and compact plant habit.
2. Vigorous growth habit.
3. Freely branching habit.
4. Early and freely flowering habit.
5. Long flowering period.
6. Double-type flowers that are purplish pink in color.
7. Good garden performance.

Plants of the new *Mandevilla* can be compared to plants of the mutation parent selection. Plants of the new *Mandevilla* differ primarily from plants of the mutation parent selection in flower form as plants of the new *Mandevilla* have double-type flowers whereas plants of the mutation parent have single-type flowers.

Plants of the new *Mandevilla* can be compared to plants of the *Mandevilla hybrida* 'Sunpa 4411', disclosed in U.S. Plant Pat. No. 33,141. In side-by-side comparisons, plants of the new *Mandevilla* differ from plants of 'Sunpa 4411' in the following characteristics:

1. Plants of the new *Mandevilla* are more compact than plants of 'Sunpa 4411'.
2. Plants of the new *Mandevilla* have shorter internodes than plants of 'Sunpa 4411'.

3. Flowers of plants of the new *Mandevilla* are double-types whereas flowers of plants of 'Sunpa 4411' are single-types.
4. Flowers of plants of the new *Mandevilla* are purplish pink in color whereas flowers of plants of 'Sunpa 4411' are purplish red in color.
5. Flower petals of plants of the new *Mandevilla* are imbricate whereas flower petals of plants of 'Sunpa 4411' are not imbricate.
6. Flower petals of plants of the new *Mandevilla* have acute apices whereas flower petals of plants of 'Sunpa 4411' have rounded apices.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 421' grown in a container.

Figure 2:
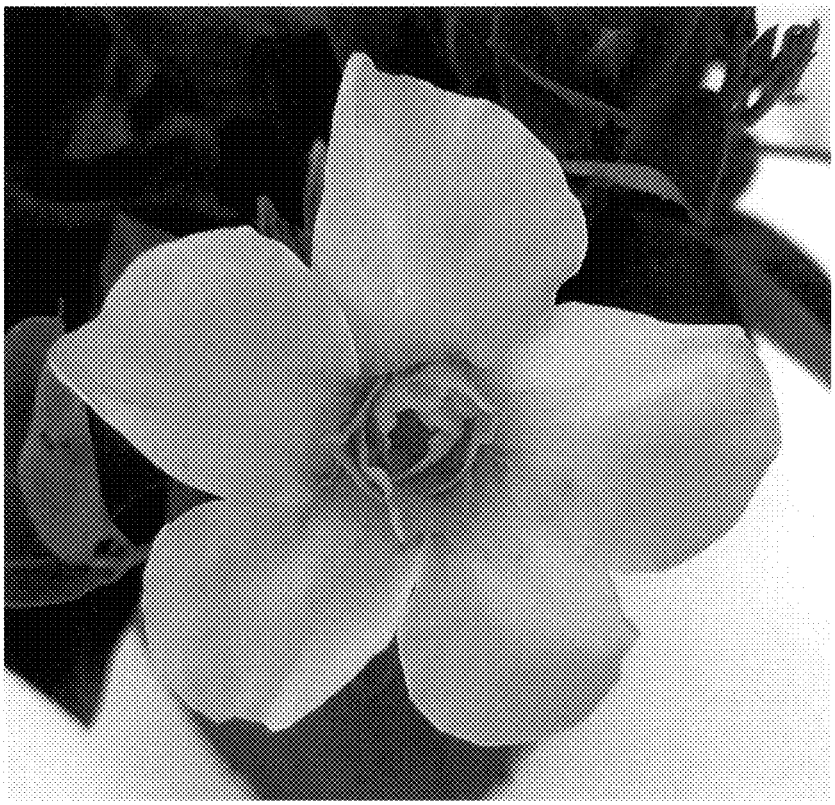

The photograph on the second sheet (FIG. 2) is a close-up view of a typical flower of 'Sunpa 421'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15 C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 421'.

Parentage: Naturally-occurring branch mutation of a proprietary selection of *Mandevilla hybrida* identified as code number MW37-mt2, not patented.

Propagation:

*Type*.—By terminal vegetative cuttings.

*Time to initiate roots, summer and winter*.—About two weeks at temperatures about 23 C to 25 C.

*Time to produce a rooted young plant, summer and winter*.—About five to six weeks at temperatures about 23 C to 25 C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright and compact plant habit; vigorous growth habit; freely branching habit; suitable for hanging baskets and garden plantings.

*Plant height*.—About 32 cm.

*Plant diameter*.—About 41 cm.

*Lateral branch description*.—Length: About 26 cm. Diameter: About 3.1 mm. Internode length: About 2 cm. Strength: Strong, flexible. Texture: Smooth, glabrous. Color, developing: Close to 138B. Color, fully developed: Close to 152B.

Leaf description:

*Arrangement and quantity*.—Decussate, simple; high density, about 22 per lateral branch.

*Length*.—About 7.6 cm.

*Width*.—About 5.4 cm.

*Shape*.—Elliptic.

*Apex*.—Acuminate.

*Base*.—Obtuse.

*Margin*.—Entire; not undulate to slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 138A. Developing leaves, lower surface: Close to 138B. Fully expanded leaves, upper surface: Close to NN137A; venation, close to NN137C. Fully expanded leaves, lower surface: Close to 137C; venation, close to 145A.

*Petioles*.—Length: About 1.4 cm. Diameter: About 2 mm. Texture, upper and lower surfaces: Smooth, glabrous. Color, upper and lower surfaces: Close to 137B.

Flower description:

*Flower type and habit*.—Double-type flowers; flowers face mostly outwardly; freely flowering habit with about three flowers per axil and typically about 18 flowers per plant.

*Natural flowering season*.—Early flowering habit, plants begin flowering about six weeks after planting rooted cuttings; long flowering period, plants flower continuously from summer until late autumn in Japan.

*Flower longevity on the plant*.—About seven to ten days; flowers not persistent.

*Fragrance*.—None detected.

*Flower buds*.—Height: About 6.1 cm. Diameter: About 1.2 cm. Shape: Rhombic. Color: Proximally, close to 150C and distally, close to 62D.

*Flowers*.—Appearance: Double-type, ten petals in two whorls; petals are imbricate. Diameter: About 6.5 cm. Depth (length): About 4.5 cm. Throat diameter, distally: About 1.6 cm. Tube length: About 1.3 cm. Tube diameter, proximally: About 6.4 mm.

*Corolla*.—Quantity and arrangement: Five petals arranged in an outer whorl and five petals in a smaller inner whorl and fused towards the base into an elongated tube; petal lobes imbricate. Petal lobe length: About 2.5 cm. Petal lobe width: About 2.3 cm. Petal lobe shape: Obovate, strongly asymmetrical. Petal lobe apex: Acute. Petal lobe margin: Entire; slightly undulate and slightly recurving. Petal lobe texture and luster, upper and lower surfaces: Smooth, glabrous; velvety; matte. Throat texture: Smooth, glabrous. Tube texture: Smooth, glabrous. Color: Petal lobe, when opening, upper surface: Close to 62A and 62B. Petal lobe, when opening, lower surface: Close to 62B and 62D. Petal lobe, fully opened, upper surface: Close to 65C and 62B; venation, similar to lamina colors; color fading to almost white, close to NN155B with subsequent development. Petal lobe, fully opened, lower surface: Close to 62C and 62D; venation, similar to lamina colors; color does not change with subsequent development. Throat: Proximally, close to 28B and distally, close to 28A; venation, close to 13B. Tube: Proximally, close to 150C and distally, close to 38D.

*Calyx*.—quantity and arrangement: Five sepals arranged in a single whorl, fused at the base; calyx, star-shaped. Sepal length: About 5.3 mm. Sepal width: About 2.1 mm. Sepal shape: Lanceolate. Sepal apex: Acute. Sepal margin: Entire. Sepal texture, upper and lower surfaces: Smooth, glabrous. Sepal color, upper surface: Close to 145B; towards the apex, tinged with close to 58A. Sepal color, lower surface: Close to 145A; towards the apex, tinged with close to 58A.

*Peduncles*.—Length: About 1.6 cm. Diameter: About 2.4 mm. Texture: Smooth, glabrous; rough. Aspect: Upright to outwardly. Color: Close to 138A.

*Pedicels*.—Length: About 4 cm. Diameter: About 2.9 mm. Texture: Smooth, glabrous; rough. Aspect: Upright to outwardly. Color: Close to N144A.

*Reproductive organs*.—Stamens: Stamen development has not been observed, all stamens transformed into inner whorl of petals. Pistils: Quantity: Typically one. Pistil length: About 1.8 cm. Style color: Close to 150B. Stigma shape: Globose. Stigma color: Close to 150A. Ovary color: Close to 149A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4 C to about 30 C.

It is claimed:

1. A new and distinct *Mandevilla* plant named 'Sunpa 421' as illustrated and described.

* * * * *